United States Patent [19]

Ripamonti

[11] Patent Number: 5,355,898
[45] Date of Patent: Oct. 18, 1994

[54] METHOD FOR INDUCING EXTRASKELETAL BONE GROWTH IN PRIMATES AND FOR SCREENING IMPLANTS THEREFOR

[75] Inventor: Ugo Ripamonti, Johannesburg, South Africa

[73] Assignee: South African Medical Research Council, South Africa

[21] Appl. No.: 889,994

[22] Filed: Jun. 2, 1992

[51] Int. Cl.$^5$ ............................................. A61B 19/00
[52] U.S. Cl. .................................................... 128/898
[58] Field of Search ............................... 128/897–899, 128/419 F

[56] References Cited

PUBLICATIONS

Richard T. Chiroff et al.; "Tissue Ingrowth of Replamineform Implants"; 1975 J. Biomed. Mater. Res. Symposium No. 6. pp. 29–45.

J. F. Piecuch; "Extraskeletal Implantation of a Porous Hydrozyapatite Ceramic"; Dec. 1982; J Dent Res 61(12): pp. 1458–1460.

T. K. Sampath et al.; "Importance of Geometry of the Extracellular Matrix in Endochondral Bone Differentiation"; Jun. 1984; The Journal of Cell Biology—vol. 98, The Rockefeller University Press 0021-9525/84/06/2192/ pp. 2192–2197.

*Primary Examiner*—Lee S. Cohen
*Assistant Examiner*—John P. Lacyk

[57] ABSTRACT

A method for screening a selected material for its osteoconductive or osteoinductive potential, which includes implanting a structure comprising the material, extraskeletally into a baboon, and examining the structure a predetermined period of time after implantation to determine what amount of bone, if any, has formed on or within the structure.

12 Claims, 17 Drawing Sheets

FIG IA
FIG IB

METHOD FOR INDUCING EXTRASKELETAL BONE GROWTH IN PRIMATES AND FOR SCREENING IMPLANTS THEREFOR

BACKGROUND OF THE INVENTION

This invention relates to a method for inducing bone growth, and a method for screening porous structures for their respective osteoinductive or osteoconductive potentials.

In recent years, interest has been shown in the osteoconductive properties of a porous hydroxyapatite substratum that is obtained after hydrothermal conversion of the calcium carbonate exoskeletal microstructure of the scleractinian reef-building corals, Porites and Goniopora. This hydroxyapatite is characterized by a relatively uniform network of interconnected channels and pores, similar to the mineralized inorganic supporting structure of living bone. Experimental evidence has established the osteoconductive properties of the porous substratum when it is implanted in orthotopic sites, and the material has been used experimentally in reconstructive operations, particularly craniofacial procedures, as an alternative to autogenous bone grafts. Studies heretofore have shown that implantation in extraskeletal sites in dogs and rodents results in penetration of fibrovascular tissue, without bone formation, which indicated that the porous hydroxyapatite does not act as a bone-inducing substratum in those animals and that ingrowth of bone within the three dimensional framework depends on close apposition of the implant with viable bone at the interfaces of the material.

However it has now surprisingly been shown that bone does form in porous hydroxyapatite that has been implanted extraskeletally in non-human primates. Details are provided in Example 1 below.

The applicant is further aware of evidence that the shape and configuration (hereinafter referred to as "the geometry") of the porous hydroxyapatite substratum can be a relevant factor in determining the osteoconductive potential of hydroxyapatite. Example 2 below describes in detail an investigation into geometric importance, and sets out the results of the investigation which lead to a conclusion that the geometry of a substratum can be critical for inducing bone growth. Thus it is conceivable that a variety of porous substances could conveniently be coated with hydroxyapatite or with other extracellular matrix components with binding affinity for osteogenin. (Osteogenin and related bone morphogenetic proteins (BMPs) are protein initiators that regulate cartilage and bone differentiation in vivo.) The applicant therefore foresees a need for a screening method whereby osteoconductive or osteoinductive potentials of various material and/or optimal geometry thereof can be tested.

SUMMARY OF THE INVENTION

According to one aspect of the invention there is provided a method for screening a selected material for its osteoconductive or osteoinductive potential, which method includes implanting a structure comprising the material, extraskeletally into a non-human primate; and examining the structure a predetermined period of time after implantation to determine what amount of bone, if any, has formed on or within the structure.

According to another aspect of the invention there is provided a method of inducing bone growth in an extraskeletal site in a primate, which method includes implanting in the site where bone is required, a porous hydroxyapatite structure.

The structure may be implanted intramuscularly in adult baboons, and examining the structure after a predetermined period of time may include removing the structure from the baboon and subjecting it to histological and histomorphometric analysis.

The method of the invention is expected to be useful not only in determining the osteoinductive or osteoconductive potentials of various materials, but also in determining the optimum shape and configuration (ie geometry) of structures for enhancing the osteoinductivity or osteoconductivity of the material.

BRIEF DESCRIPTION OF THE DRAWINGS

The invention is now described by way of example and with reference to the following Figures:

FIGS. 1A, 1B, 2A, 2B, 2C, 2D, 3A, 3B, 3C and 3D are photomicrographs at the following magnifications, of specimens prepared from implants harvested at three months:

1A — ×20 magnification
1B — ×50
2A — ×50
2B — ×200
2C — ×400
2D — ×400
3A — ×20
3B — ×50
3C — ×100
3D — ×50

Figure 2A:
Figure 2B:
Figure 2C:
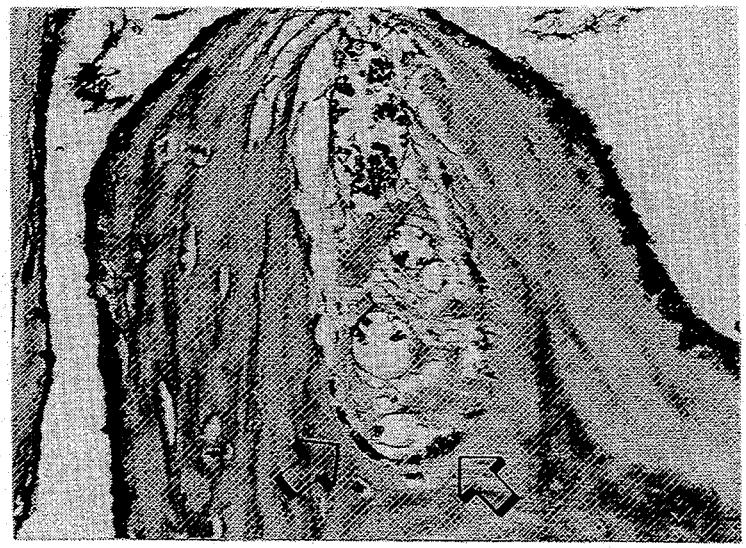
Figure 2D:
Figure 3A:
Figure 3B:
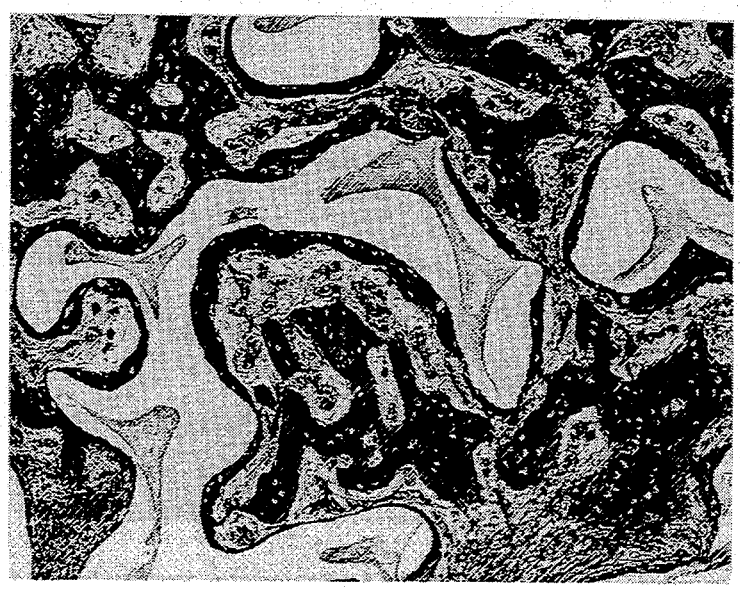
Figure 3C:
Figure 3D:
Figure 4A:
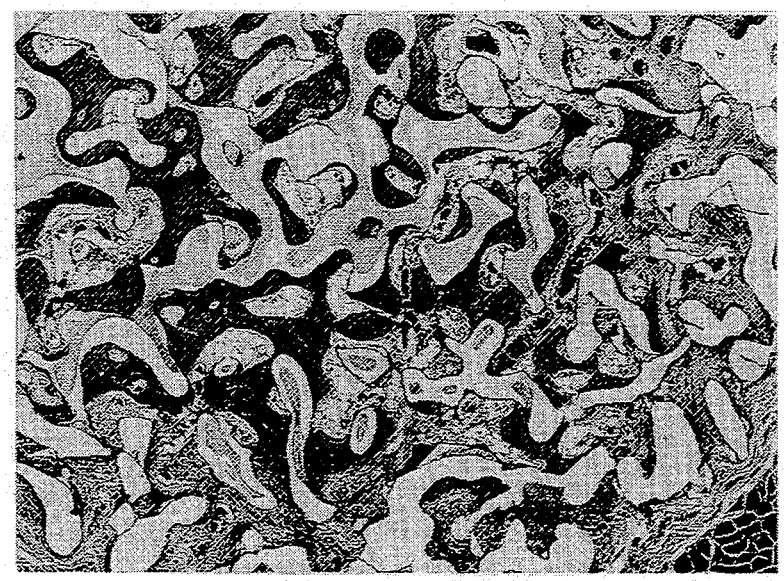
Figure 4B:
Figure 4C:
Figure 4D:
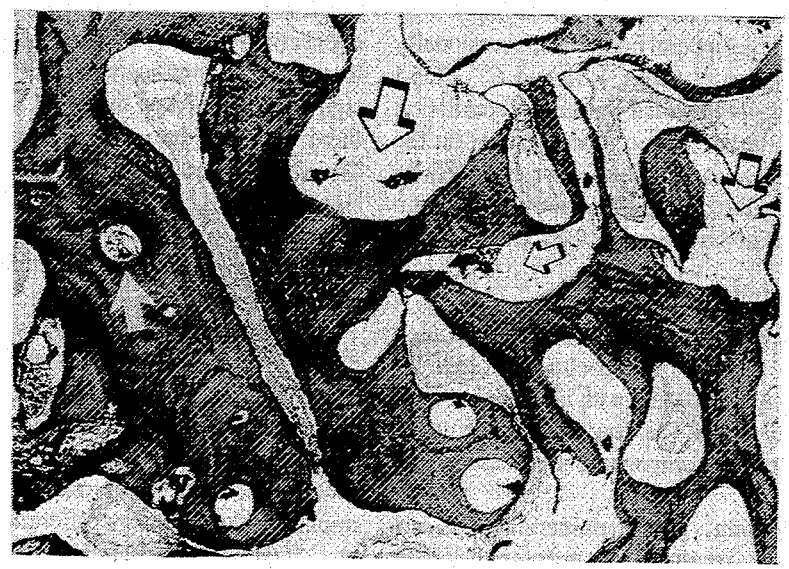
Figure 5A:
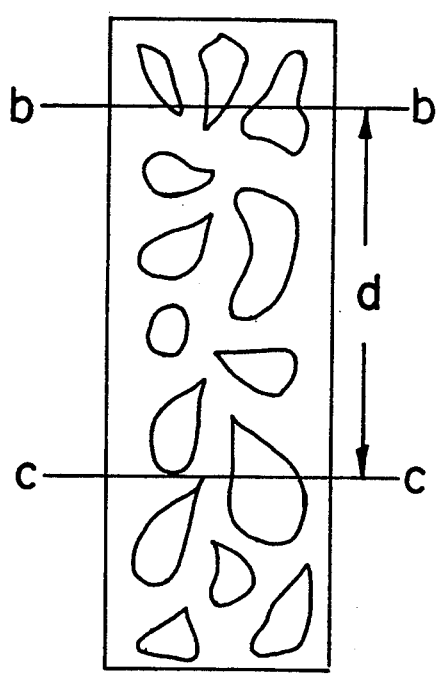
Figure 5B:
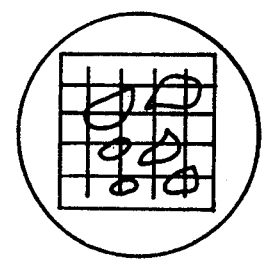
Figure 5C:
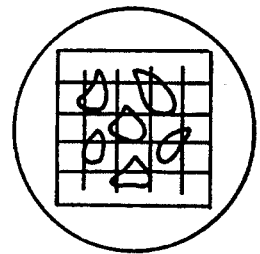

FIGS. 4A and 4B are photomicrographs at different magnifications (i.e. ×20 and ×50) of a specimen prepared from an implant harvested at six months;

FIGS. 4C and 4D are photomicrographs at different magnifications (i.e. ×20 and ×50) of a specimen prepared from an implant harvested at nine months;

FIG. 5A is a schematic representation of an hydroxyapatite rod of 200 or 500 μm pore size;

FIG. 5B is a schematic representation of a cross-section through the hydroxyapatite rod of FIG. 5A, taken at b—b;

FIG. 5C is a schematic representation of a cross-section through the hydroxapatite rod of FIG. 5A, taken at c—c.

Figure 6A:
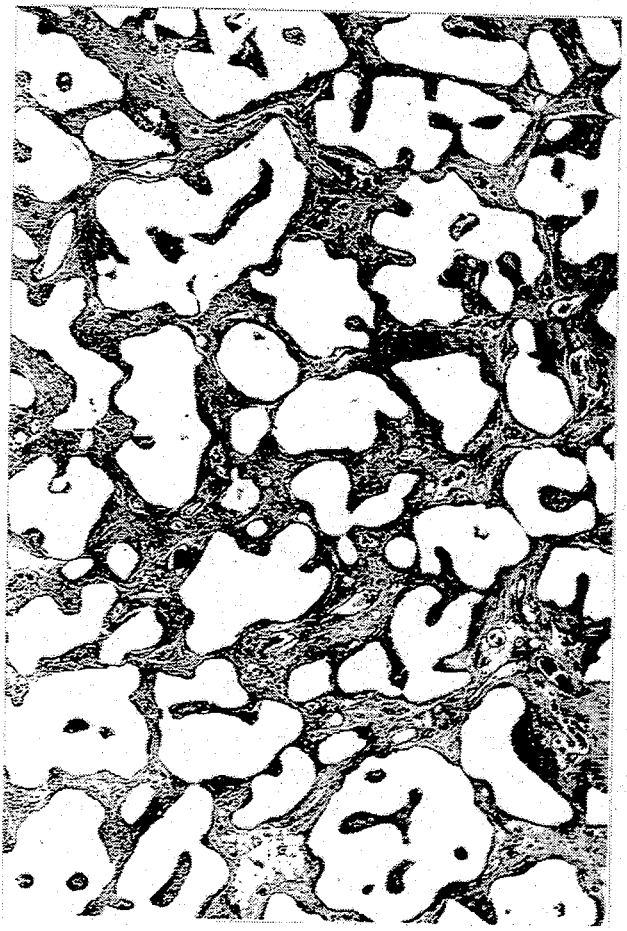
Figure 6B:
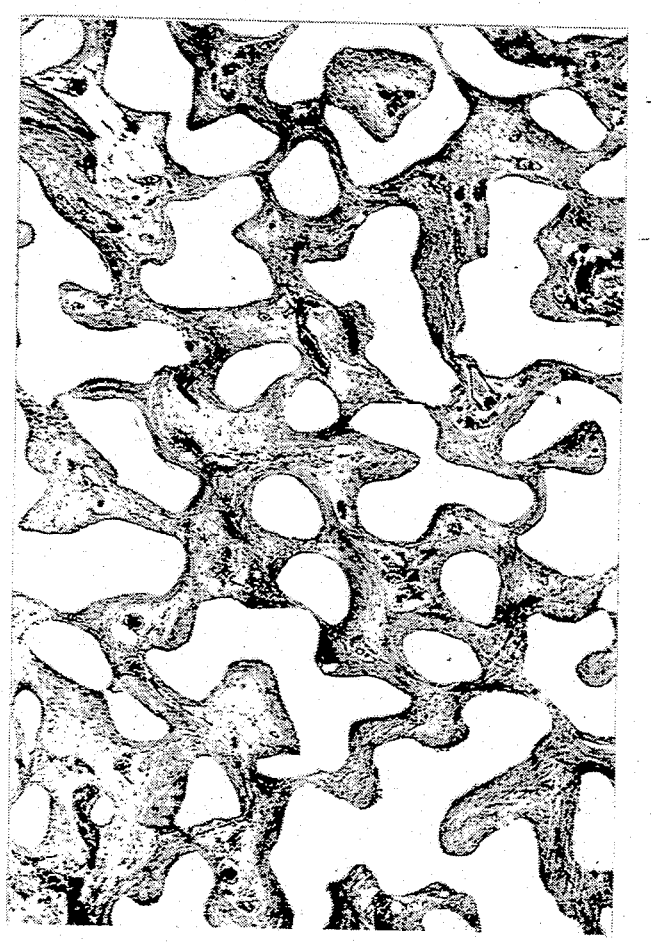
Figure 6C:
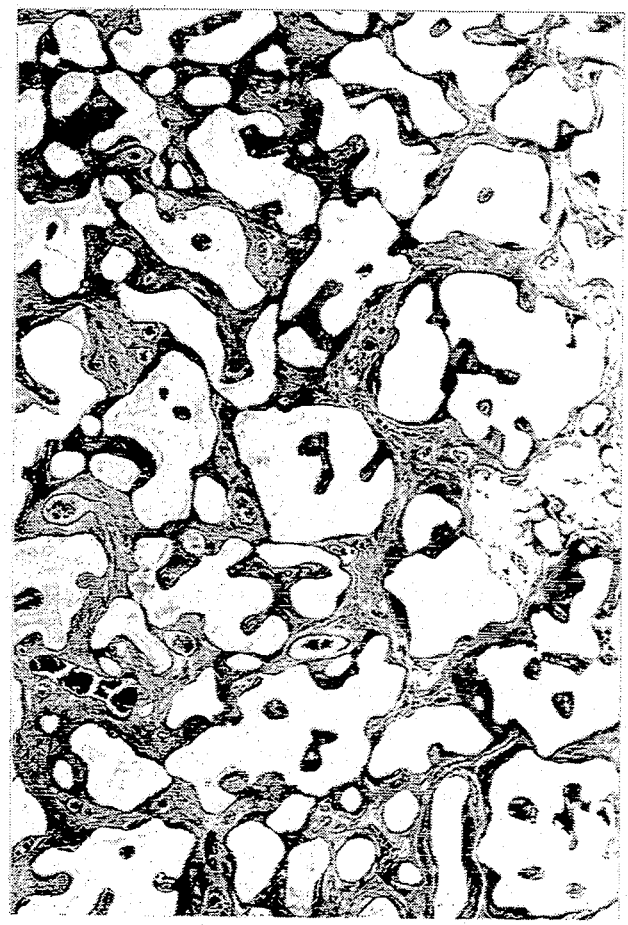
Figure 6D:
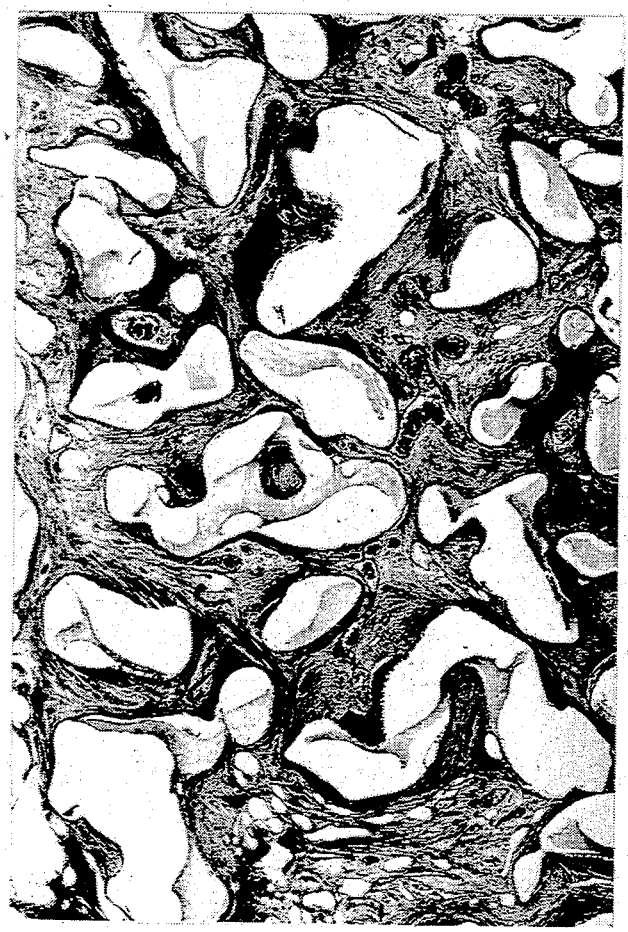
Figure 7A:
Figure 7B:
Figure 7C:
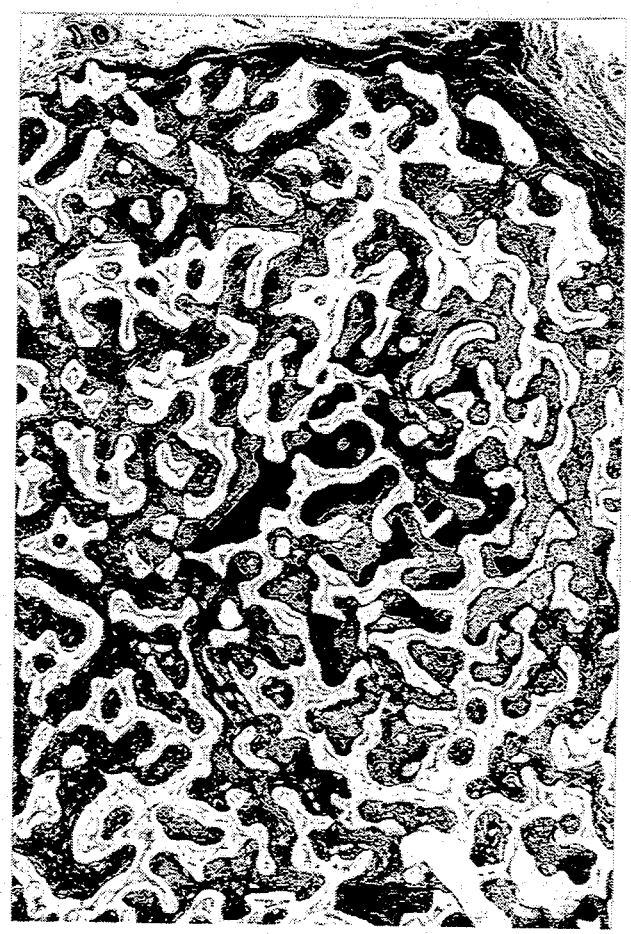
Figure 7D:
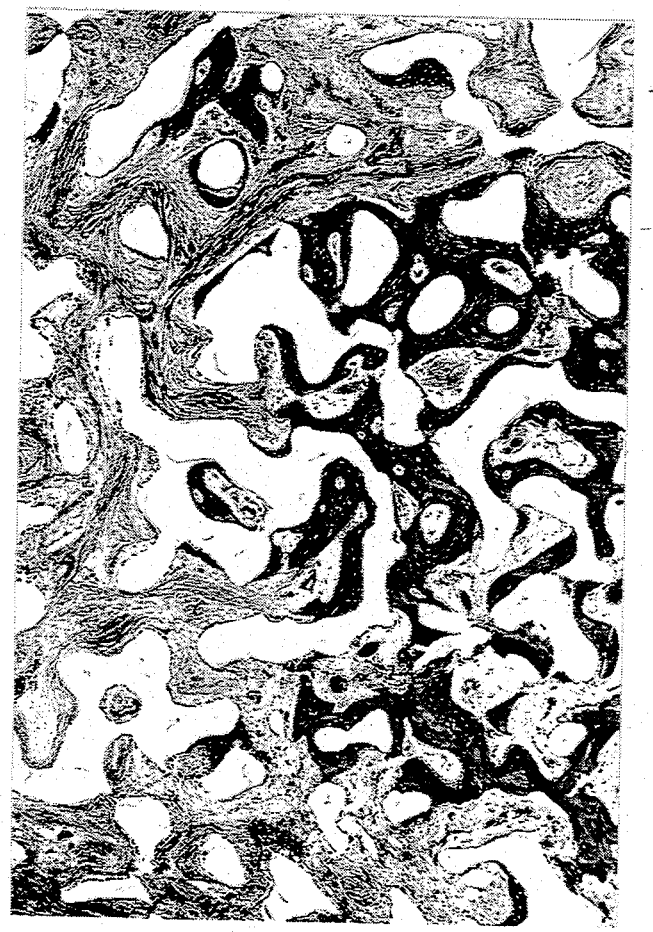

FIGS. 6A and 6B are photomicrographs (×20) of specimens prepared from implants of granular hydroxyapatite, 200 and 500 μm pore size respectively, harvested at day 60;

FIGS. 6C and 6D are photomicrographs (×20) of specimens prepared from implants of granular hydroxyapatite, 200 and 500 μm pore size respectively, harvested at day 90;

FIGS. 7A and 7B are photomicrographs (×20) of specimens prepared from implants of hydroxyapatite rods, 200 and 500 μm pore size respectively;

FIGS. 7C and 7D are photomicrographs (×20) of specimens prepared from implants of hydroxyapatite rods, 200 and 500 μm pore size respectively, harvested at day 90.

Figure 8:
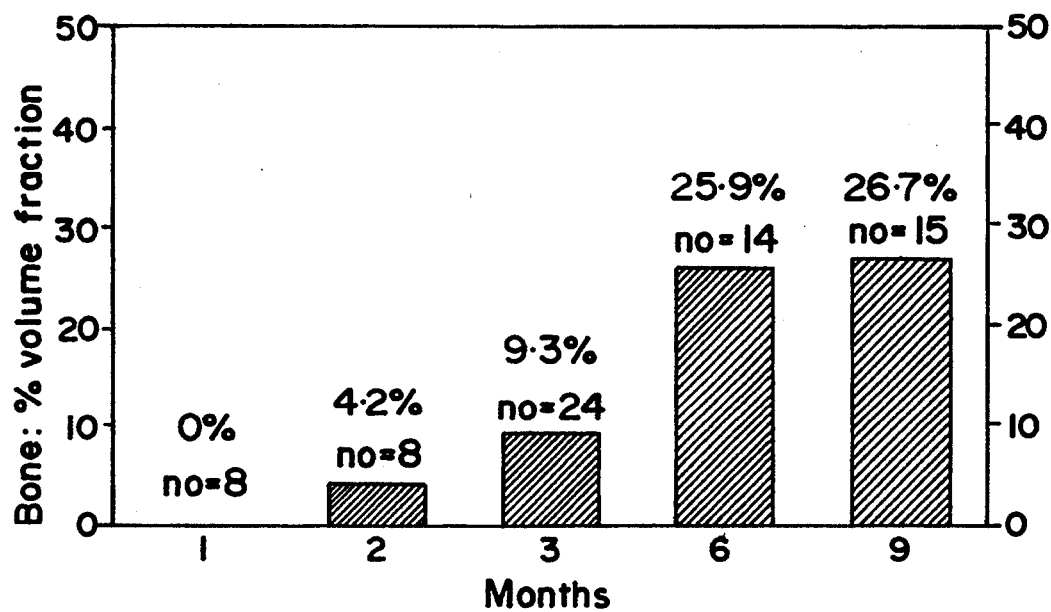

FIG. 8 is a graph representing the amount of bone that formed in hydroxyapatite rods implanted extraskeletally in baboons after one, two, three, six and nine month(s) respectively.

DETAILED DESCRIPTION OF THE INVENTION

EXAMPLE 1

Materials and Method

Twenty-four clinically healthy adult male Chacma baboons (Papio ursinus) having normal hematological and biochemical profiles and skeletal maturity and weighing a mean of 27.8±3.3 kg (range, 22.4 to 36 kg) were selected for experimentation. The animals were housed individually in a region which is about 1800 meters above sea level. The rooms in which the animals were housed were kept under slight negative pressure (−25 kilopascals), with controlled ventilation (eighteen filtered air changes each hour), temperature (22°±2° C.), humidity (40±10%), and photoperiod (lights on from 6 am to 6 pm).

Implants of Hydroxyapatite

Implants of porous hydroxyapatite were specially prepared by Interpore International (Irvine, Calif.) to the specifications of the protocol. A hydrothermal chemical exchange with phosphate converted the original microstructure of the calcium carbonate exoskeleton of the Goniopora coral into an inorganic replica of hydroxyapatite. Implants consisted of rods of porous hydroxyapatite that measured 20 mm in length and 7 or 5 mm in diameter. The solid trabeculae of the framework averaged 130 $\mu$m in diameter, and their interconnections averaged 220 $\mu$m in diameter. The average porosity was 600 $\mu$m, and their interconnections averaged 260 $\mu$m in diameter (Interpore 500). Before implantation, the rods of hydroxyapatite were sterilized in an autoclave at 115° C. for 20 minutes.

Operative Procedures and Intramuscular Implantation

On the evening before the operation, food was withheld from the animals, but they had continued access to water ad libitum. On the date of the operation, the animals were immobilized with an intramuscular injection of phencyclidine hydrochloride (1 mg/kg of body weight) or ketamine hydrochloride (8 mg/kg of body weight) and anesthetized with intravenous administration of thiopentone sodium (15 mg/kg of body weight). Anesthesia was maintained with halothane vapor in 100% oxygen following orotracheal intubation. A total of 48 rods of hydroxyapatite were implanted bilaterally in ventral and dorsal intramuscular pouches that had been created with sharp and blunt dissection in the rectus amominis and in the latissimus or longissimus dorsi after partial reflection of the trapezius.

An equal number of rods of hydroxyapatite of 7 mm and 5 mm diameter were distributed between the two sites of implantation.

Two rods of hydroxyapatite were implanted in each animal, one rod in an anterior pouch and one rod in a posterior pouch. To close the pouches after implantation of the hydroxyapatite, the fasciae and the superficial tissues were repaired in layers with atraumatic resorbable sutures.

After the operation, benethamine and procaine penicillins were administered by intramuscular injection. Post-operatively, pain was controlled with intramuscular injection of buprenorphine hydrochloride (0.3 mg). The individually housed animals were kept under daily clinical observation. They were fed soft food that consisted of basic proteins, fat, carbohydrates, fibers, calcium, iron, phosphates, and vitamins (thiamine, riboflavin, and nicotinic acid), mixed in a ratio of 3:1 with a protein-vitamin-mineral dietary supplement. This was later supplemented with commercial monkey cubes.

Harvesting and Processing of Tissue

The animals were immobilized and anesthetized; they were then killed with an intravenous overdose of pentobarbitone: eight animals at three months, eight at six months, and eight at nine months after the operation.

The harvested implants, with surrounding soft tissues, were fixed in 10% formol-buffered saline solution, decalcified in formic acid-sodium citrate solution, and double-embedded in celloidin and paraffin wax. 5 $\mu$m serial sections were cut in a plane perpendicular to the long axis of the rods of hydroxyapatite and were stained with toluidine blue.

Histological and Histomorphometric Analysis

From each specimen, a minimum of four levels were available for analysis. Examination of the whole material showed remarkable and unexpected differentiation of bone within the porosities of the hydroxyapatite. Four patterns of structural organization were consistently recognized:

(1) fibrous connective tissue with a pronounced cellular and vascular component; (2) fibrous connective tissue that was characterized by condensation of collagen fibers at the interface of the hydroxyapatite; (3) morphogenesis of bone; and (4) remodeling of bone, formation of lamellar bone, and differentiation of bone marrow. Accordingly, the histomorphometric analysis was designed to quantitate, withthe point-counting technique, these different histological patterns within the porous spaces. A calibrated square integration plate II (Carl Zeiss, Thornwood, N.Y.) with 100 lattice points was used to calculate the fractional volumes (in %) and the derived absolute cross-sectional area (in mm$^2$) of each histological component: fibrovascular tissue, connective-tissue condensation, bone, bone marrow, and hydroxyapatite substratum.

Sections were analyzed in a Univar light microscope (Reicheft, Vienna, Austria), magnified forty times, with the Zeiss graticule superimposed over the center of the specimen. A single central field of 7.84 mm$^2$ was analyzed for each section. Histomorphometric analysis was performed on two sections from the same specimen at two different levels, 100 or 150 $\mu$m apart. The connective-tissue condensation was analyzed at the three-month time-interval only.

Statistical Analysis

The data were analyzed with a computer (Model 3083 J24, IBM), with the Statistical Analysis System. For each pattern of structural organization, the model design analyzed the effects and interactions of five independent class variables: the individual response of the animal (nested with time), the time-period (three, six, or nine months), the site of implantation (anterior or posterior), the diameter of the rods of hydroxyapatite (7 or 5 mm), and the histological levels of the histomorphometric analysis (two levels, 100 or 150 $\mu$m apart).

Results

Clinically, healing was uncomplicated in all animals, and there was no evidence of rejection of the implants. Immediately after harvest, macroscopic examination showed optimum incorporation of the implants within the recipient muscular tissues, without fibrous encapsulation. Three implants were spoiled during histological preparation, leaving forty-five implants of hydroxyapatite. Histomorphometry was performed on a total of 90 fields.

Morphological Analysis

The consistent recognition of four different patterns of structural organization was briefly described in the areas of the tissue components are presented in Table II.

TABLE I

| | | Hydroxyapatite | | | | |
|---|---|---|---|---|---|---|
| Period | No | Hydroxy-apatite | Bone | Connect.-Tissue Condens. | Fibrovasc. | Marrow |
| 3 mos. | 16 | 37.7 ± 1.0 | 9.2 ± 2.1 | 19.2 ± 2.5 | 31.8 ± 1.8 | 2.1 ± 0.7 |
| 6 mos. | 14 | 34.7 ± 1.3 | 25.9 ± 2.2 | ND | 32.6 ± 2.4 | 6.9 ± 1.3 |
| 9 mos. | 15 | 30.4 ± 1.2 | 26.7 ± 2.1 | ND | 32.1 ± 3.1 | 10.8 ± 2.1 |
| Mean | | 34.4 ± 0.7 | 20.2 ± 1.5 | | 32.1 ± 1.4 | 6.5 ± 0.9 |

*Mean and standard error of the mean
ND = Not determined

Materials and Methods section. Two distinct structural features characterized the connective tissue that invaded the porous spaces of the implants of hydroxyapatite: a vascular component within a cellular, loose connective-tissue matrix, and the differentiation of a peculiar pattern of mesenchymal condensation and alignment of connective-tissue fibers, mostly in direct contact with the surfaces of the hydroxyapatite (FIGS. 1, A and B). Osteocyte-like cells were embedded within a tissue that had intermediate features between fibrous connective tissue and bone (FIGS. 2, A through D). Large vessels had invaded the connective-tissue matrix, penetrating the porosities of the hydroxyapatite (FIGS. 1, A and 2, A through D), and occasionally the vascular walls were almost in direct contact with the hydroxyapatite substratum (FIG. 2, A). In the Figures, the empty white spaces represent the hydroxyapatite framework after decalcification during histological processing.

At three months, bone had developed in twenty-four specimens (77%). The amount of bone ranged from slight to florid and mainly occupied the center of the implant of hydroxyapatite. Bone was mostly in direct contact with the hydroxyapatite substratum, and contiguous layers of osteoblasts lined newly deposited bone matrix (FIGS. 3, B and C). The structural organization ranged from lamellar (FIG. 3,D) to delicate trabecular-like woven bone invading the highly vascularized connective-tissue matrix (FIGS. 3, A and B).

At six and nine months, morphogensis of bone had occurred in twenty-four (92%) and thirty-one (100%) of the specimens, respectively. Although the amount of bone varied considerably, in several specimens an extensive amount of bone had developed, filling large portions of the porosities, both at the center and at the periphery (FIGS. 4, A through D). Vascular spaces with the features of haversian canals penetrated the remodeled bone supporting osteonic-like structures (FIG. 4, D). Whereas the lamellar bone was mainly localized to the central areas of the implants of hydroxyapatite, the newly developing woven bone extended toward the peripheral porosities, occasionally culminating in total penetration (FIGS. 4, A and C) Florid deposition of bone was accompanied by the differentiation of marrow (FIG. 4, B). Remodeling of bone resulted in the formation of large marrow cavities that were confined by relatively thin trabecular-like osseous structures, laminating the substratum and populated by sparse osteoblast-like cells.

Histomorphometric Analysis

The volume fraction compositions at each observation period are summarized in Table I for the specimens of hydroxyapatite. The derived absolute cross-sectional

TABLE II

MEAN ABSOLUTE CROSS-SECTIONAL AREAS (IN SQUARE MILLIMETERS) OF TISSUE COMPONENTS IN SPECIMENS OF HYDROXYAPATITE

| | | Hydroxyapatite | | | | |
|---|---|---|---|---|---|---|
| Period | No | Hydroxy-apatite | Bone | Connect.-Tissue Condens.* | Fibrovasc. | Bone Marrow |
| 3 mos. | 16 | 2.95 | 0.72 | 1.51 | 2.49 | 0.16 |
| 6 mos. | 14 | 2.72 | 2.03 | ND | 2.56 | 0.54 |
| 9 mos. | 15 | 2.38 | 2.09 | ND | 2.51 | 0.84 |
| Mean | | 2.70 | 1.58 | | 2.51 | 0.51 |

*ND = not determined

Histological processing, after demineralization and double-embedding in wax, resulted in an average shrinkage of the cross-sectional diameter of 23% for the 7 mm diameter rods of hydroxyapatite, so that the average area of the sections was 22.7 mm$^2$. The corresponding values for the 5 mm diameter implants were 21% and 12.3 mm$^2$. The histomorphometric field for the 7 mm and 5 mm specimens included 35 and 65% of the section, respectively. The amount of bone increased significantly between three and six months but there was no additional significant increase at nine months. The volume fraction of fibrovascular tissue did not change significantly between the various periods of observation. The amount of bone marrow increased significantly between three and six months and again between six and nine months.

Separate analyses for the site of implantation and the diameter of the rods of hydroxyapatite showed that, on average, a greater amount of bone formed in the 7 mm implants, regardless of the site of implantation. At nine months, however, equal amounts of bone were found in both the 7 mm and the 5 mm implants. No significant differences were found between the two diameters with regard to the hydroxyapatite framework. On average, more bone formed in the anterior specimens, although the difference with regard to the site of intramuscular implantation was significant only in the 7 mm implants. More bone marrow also developed in the anterior implants. Inversely, significantly more fibrovascular tissue was found in the posterior implants. The volume fraction compositions in relation to the diameter of the rods of hydroxyapatite and to the site of implantation are presented in Tables III and IV. The analysis failed to show any significant difference between the two histological levels, 100 or 150 μm apart, with regard to the amount of bone, the extent of connective-tissue condensation, fibrovascular invasion, or differentiation of bone marrow (data not shown).

TABLE III

VOLUME FRACTION COMPOSITION (IN %) OF FIVE AND 7 mm DIAMETER SPECIMENS OF HYDROXYAPATITE*

Five-Millimeter-Diameter Specimens

| Period | No. | Hydroxy-apatite | Bone | Connect.-Tissue Condens. | Fibrovasc. | Bone Marrow |
|---|---|---|---|---|---|---|
| 3 mos. | 13 | 38.6 ± 1.8 | 5.9 ± 2.1 | 21.2 ± 2.3 | 33.9 ± 1.4 | 0.5 ± 0.3 |
| 6 mos. | 10 | 34.9 ± 1.3 | 22.1 ± 2.6 | ND | 36.4 ± 3.0 | 6.5 ± 1.6 |
| 9 mos. | 9 | 32.1 ± 1.0 | 27.6 ± 1.5 | ND | 28.2 ± 2.8 | 12.1 ± 2.4 |

Seven-Millimeter-Diameter Specimens

| No. | Hydroxy-apatite | Bone | Connect.-Tissue Condens. | Fibrovasc. | Bone Marrow |
|---|---|---|---|---|---|
| 19 | 36.1 ± 1.0 | 13.4 ± 1.7 | 14.6 ± 2.4 | 32.9 ± 1.0 | 3.0 ± 0.7 |
| 16 | 35.4 ± 1.2 | 27.5 ± 1.8 | ND | 31.4 ± 2.0 | 6.1 ± 1.1 |
| 22 | 31.5 ± 1.1 | 27.9 ± 1.9 | ND | 29.9 ± 2.6 | 10.6 ± 1.7 |

*Mean and standard error of the mean.
ND = not determined.

TABLE IV

VOLUME FRACTION COMPOSITION (IN %) OF SPECIMENS OF HYDROXYAPATITE IMPLANTED IN THE RECTUS ABDOMINIS (ANTERIOR SITE) AND THE LATISSIMUS DORSI (POSTERIOR SITE)*

Anterior Site

| Period | No. | Hydroxy-apatite | Bone | Connect.-Tissue Condens. | Fibrovasc. | Bone Marrow |
|---|---|---|---|---|---|---|
| 3 mos. | 16 | 35.3 ± 0.9 | 12.6 ± 2.0 | 18.7 ± 2.4 | 30.5 ± 1.6 | 2.9 ± 0.9 |
| 6 mos. | 11 | 35.5 ± 1.4 | 26.0 ± 3.1 | ND | 30.5 ± 3.1 | 8.4 ± 1.5 |
| 9 mos. | 16 | 31.1 ± 1.1 | 29.9 ± 1.1 | ND | 24.0 ± 2.2 | 14.9 ± 1.9 |

Posterior Site

| No. | Hydroxy-apatite | Bone | Connect.-Tissue Condens. | Fibrovasc. | Bone Marrow |
|---|---|---|---|---|---|
| 16 | 38.8 ± 1.2 | 8.6 ± 1.9 | 15.8 ± 2.5 | 36.2 ± 2.0 | 1.0 ± 0.4 |
| 16 | 35.0 ± 1.1 | 24.9 ± 1.4 | ND | 35.5 ± 1.9 | 4.7 ± 1.1 |
| 15 | 33.3 ± 1.9 | 25.6 ± 2.6 | ND | 35.2 ± 3.2 | 6.8 ± 1.7 |

*Mean and standard error of the mean.
ND = not determined.

The volume fraction of the hydroxyapatite substratum ranged from 23% to 50% (mean, 37.1%) at three months, from 23% to 51% (mean, 35.2%) at six months, and from 17 to 46% (mean, 31.7%) at nine months. Although the mean values differed, the hydroxyapatite framework did not change significantly between three and six months. However, the difference between six and nine months was significant, indicating biodegradation, although moderate, over time (5.4% in six months).

The histomorphometric analysis showed a considerable variation (range, 17 to 51%) in the volume fractions of the hydroxyapatite framework between different specimens. This variation was found to have a significant effect on the amount of bone formation within the porosities of the hydroxyapatite. The analysis showed a negative correlation (Pearson correlation coefficient, $r = -0.581$) between values for hydroxyapatite and those for bone. Regression analysis showed that the relationship was linear with a negative slope. Plotting of values for bone against those for hydroxyapatite indicated that higher and reproducible generation of bone occurred in hydroxyapatite substrata, with volume fractions ranging from 23 to 40%.

Discussion

The above results firmly establish that, when they are implanted extraskeletally in adult baboons, porous hydroxyapatite is capable of inducing differentiation of bone in direct contact with the hydroxyapatite substratum.

The histological analysis indicated that the central core of the hydroxyapatite was the nucleus for the initial morphogenetic events leading to differentiation of bone. There was extensive remodeling followed by formation of lamellar bone as early as three months after implantation, and it was most evident at six and nine months. The constant observation of a morphogenetic nucleus that was mainly localized to the center of the implant supports an interpretation of a time-related centrifugal pattern of tridimensional growth of bone, extending to the periphery of the implants and occasionally culminating in total penetration (FIGS. 4, A through D).

The correlation between the magnitude of induced bone and a specific range of values of the substratum framework suggests that the geometric configuration of the substratum influences the extent of bone formation, perhaps by providing porous spaces that are architecturally more conducive to deposition of bone.

Variation in the amount of bone formation within different specimens may be the result of subtle differences in the surface characteristics of the substratum and in the time-related release of putative adsorbed osteogenin interacting with a variable source of responding mesenchymal cells. Indirectly, this interpretation is supported by the quantitative differences in bone formation between sites of implantation. The variation between animals was interpreted as being the result of individual differences in the availability of a continuous flow of undifferentiated cells that are potentially capable of transformation toward osteoblastic cell-lines. Differences in the amount of bone within diameter configurations may reflect a sampling error resulting from the inclusion of larger peripheral areas during the quantitation of the sections from the five-millimeter-diameter specimens.

The significant difference between the values for the hydroxyapatite framework at six and nine months clearly indicates that there was biodegradation of the substratum over time and suggests that an incomplete conversion of carbonate to apatite occurred.

EXAMPLE 2

Materials and Methods

Eight clinically healthy sub-adult Chacma baboons (*Papio ursinus*) with a mean weight of 22.1 kg (range: 20.3 to 23.3 kg) and with normal hematologic and biochemical profiles were selected. Housing conditions and diets were as previously described.

Hydroxyapatite Substrata

Four different configurations of porous hydroxyapatite were specially prepared by Interpore International (Irvine, Calif.) to the specifications of the protocol (Table I). Substrata consisted of blocks in rod configuration (20 mm in length and 7 mm in diameter), and granules (400-620 μm in diameter) of porous hydroxyapatite. Before implantation, the hydroxyapatite in both rod and granular configuration were sterilized in an autoclave at 115° C. for 30 minutes. Implants of porous granular hydroxyapatite were preformed by adding 1 mg of chondroitin-6-sulfate (Sigma Chemical Co., St. Louis, Mo.) and 2 mg of baboon type I collagen to 400 mg of granular hydroxyapatite per implant, dispensed in individual sterile polypropylene tubes. Type I collagen was prepared from the extracellular matrix of baboon bone as described. Briefly, pepsin extracts of insoluble collagenous bone matrix in 0.5M acetic acid were dialyzed against 01, M acetic acid in a Spectropor tube with 10,000 MW cut off. After dialysis against 0.05M sodium phosphate dibasic and centrifugation at 12,000 rpm, the precipitate was redissolved in 0.5M acetic acid, and redialyzed extensively against sodium phosphate dibasic. The final precipitate was lyophilized and collagen type I was dissolved in 0.5M acetic acid with a concentration of 5 mg per ml. After absolute ethanol precipitation and centrifugation, the implants of porous granular hydroxyapatite were washed 3 times with chilled 85% ethanol, dried in a SpeedVac SC100 concentrator (Savant Instruments, Farmingdale, N.Y.) and stored at 4° C. until implantation.

Screening in Baboons—operative procedures and intramuscular implantation.

Anesthesia and surgical procedures in the baboons were as previously described. A total of 32 hydroxyapatite rods and 64 granular hydroxyapatite implants were implanted bilaterally in ventral intramuscular pouches created by sharp and blunt dissection in the *rectus abdominis* (Table V). Each animal was implanted with four rods (two of 200 and two of 500 μm pore size) and eight granular implants (four of 200 and four of 500 μm pore size). While superiorly and laterally surrounded by muscular tissue, the implants rested on the peritoneal fascia. The muscular fascia and the superficial tissues were repaired in layers with atraumatic resorbable sutures. Postoperative pain was controlled by intramuscular buprenorphine hydrochloride (0.3 mg). Individually housed animals were monitored and fed as described above.

TABLE V

Configuration and Specification of Hydroxyapatite Substrata

| Substratum | Porosity μm | Geometric configuration | Dry weight mg/implant | No. |
|---|---|---|---|---|
| Hydorxyapatite | 200 | Granules* | 400 | 32 |
| Hydroxyapatite | 200 | Rods* | 740 ± 90 | 16 |
| Hydroxyapatite | 500 | Granules* | 400 | 32 |
| Hydroxyapatite | 500 | Rods* | 590 ± 12 | 16 |

*Replica from genus Porites[35]: average porosity of scleroseptal channels 230 μm, fenestrated interconnections 190 μm, average void fraction 60% (Interpore 200)[54].
*Replica from genus Goniopora[35]: average porosity of scleroseptal channels 600 μm, fenestrated interconnections 260 μm, average void fraction 70% (Interpore 500)[54].

Tissue Harvest and Histology

Immobilized and anesthetized animals were killed at day 60 and 90 after operation with an intravenous overdose of pentobarbitone, four animals per observation period. At harvest, implants of granular hydroxyapatite showed a dome-shaped configuration with the flat surface attached to the peritoneal fascia. Harvested implants were cleared of adhering soft tissues, fixed in 10 percent neutral buffered formaldehyde, decalcified in formic acid-sodium citrate solution, and double embedded in celloidin and paraffin wax. Serial sections 5 μm thick, were cut in a plane perpendicular to the long axis of the hydroxyapatite rods. Serial sections, 5 μm thick, were cut longitudinally along the flat surface of the specimens of granular hydroxyapatite. Sections were stained with 0.1 percent toluidine blue in 30 percent ethanol or with the Goldher's trichrome.

Histomorphometric Analysis

A calibrated Zeiss Integration Platte II (Reicheft AG, Austria) with 100 lattice points was used to calculate, by point "counting technique", the fractional volumes (in percent) of each histologic component: soft tissue (including vascular and marrow tissues), bone, and the framework of the hydroxyapatite substratum. Sections were analyzed in an Univar light microscope as described above. In specimens of hydroxyapatite rods, histomorphometry was performed on two sections (b and c respectively) from the same specimen, which sections were a distance (d) of approximately 11 mm apart, as shown in FIG. 5. In addition, after analysis, each section was rotated through 180° about the central axis and re-analyzed to miniminss sampling error.

Statistical Analysis

The data were analyzed on an IBM 3083 J24 computer with the Statistical Analysis System.

Results

Histology

At harvest, the implants were firmly attached to the fascia and the overlying muscles. At day 60, bone did not form in any specimen of granular hydroxyapatite of both 200 and 500 μm pore size (FIGS. 6, A, B). There was differentiation of a dense but vascular connective tissue. In the Figures, the empty spaces and lacunae represent the framework of the hydroxyapatite removed during calcification. At day 90, bone did not form in specimens of granular hydroxyapatite of 200 μm pore size. Instead, a relatively dense and highly vascular connective tissue developed within the porous spaces between and within granules (FIG. 6, C). However, at day 90, two specimens of granular hydroxyapatite of 500 μm pore size showed the presence of minimal amounts of bone in direct opposition to the hydroxyapatite (FIG. 6, D). In contrast, bone differentiation did occur in hydroxyapatite specimens in rod configuration of both 200 and 500 μm pore size as early as day 60 after implantation (FIGS. 7, A, B). There was differentiation of bone within the central core of the specimens and in direction opposition to the substratum. At day 90, bone formation was often substantial and consistently found within the central core of the sections (FIGS. 7, C, D). Generation of bone marrow was observed.

Histomorphometry

The volume fraction of tissue components in hydroxyapatite specimens of granular and rod configuration at each observation period are presented in Tables VI and VII. At day 60 and 90, on average, greater amounts of bone formed in hydroxyapatite rods of 500 μm pore size when compared to rods of 200 μm pore size. This difference, however, was not significantly different. This may reflect the considerable variation in biologic response between different animals. The analysis showed a significant difference between the two histologic levels analyzed for histomorphometry. In both hydroxyapatite rods of 200 and 500 μm pore size, greater amounts of bone were found at level b when compared to level c (Tables VI and VII). In hydroxyapatite rods of 200 μm pore size, the volume fraction of bone ranged from 0 to 9 percent, and from 0 to 17 percent at day 60 and 90 respectively. In hydroxyapatite rods of 500 μm pore size, the corresponding values were 0 to 13 percent and 0 to 24 percent respectively. The volume fraction of the hydroxyapatite substratum was greater in rods of 200 μm pore size when compared to rods of 500 μm pore size (Tables VI and VII). It is noteworthy that the amount of bone that formed in hydroxyapatite rods of 500 μm pore size is almost identical to results obtained in Example 1:9.3 percent in the present study compared to 9.2 percent for Example 1.

along the longitudinal axis of the rods. Histologic examination showed the presence of substantial bone within the central core of the sections, but limited bone deposition at the periphery of the implants, confirming the histomorphometric results.

Discussion

Example 1 provides evidence that hydroxyapatite in rod configuration and an average pore size of 500 μm are conducive to cellular and extracellular interactions leading to a unique pattern of bone differentiation in extraskeletal sites of adult baboons. In the present example (i.e. Example 2), this hydroxyapatite-induced osteogenesis model in primates was used to study the effect of geometry and pore size of the substratum on bone morphogenesis, and to determine more accurately the time of initiation of bone formation.

With the exception of an island of bone that formed in two implants of granular hydroxyapatite of 500 μm pore size, bone differentiation occurred only in hydroxyapatite with a rod configuration of either pore size. The results described in this report indicate that the geometric configuration of the porous substratum positively influences cell specific differentiation and directs the expression of the osteogenic phenotype. It is noteworthy that bone did not differentiate at the level of the most peripheral porous spaces of the implanted hydroxyapatite rods. This suggests that the molecular and cellular mechanisms initiating bone differentiation in hydroxyapatite substrata may not have equal access to all porous spaces.

The results indicate that bone differentiation in hydroxyapatite in rod configuration occurs by day 60 after intramuscular implantation. This observation, combined with the observed lack of bone differentiation in specimens harvested at day 30 after implantation[49], suggests that the initiation of bone formation may depend on a critical concentration of endogenously produced BMPs adsorbed onto the hydroxyapatite surface.

FIG. 8 graphically represents the combined results of Examples 1 and 2 and of a previous study. It provides

TABLE VI

Volume Fraction (%) of Tissue Components in Hydroxyapatite Specimens Implanted in the Rectus Abdominis of 4 Baboons and Harvested at day 60

| | Granular 200 μm | Granular 500 μm | Rod 200 μm | | Rod 500 μm | |
| --- | --- | --- | --- | --- | --- | --- |
| | | | Level b | Level c | Level b | Level c |
| BONE | 0.0 | 0.0 | 2.8 ± 1.0 | 0.3 ± 0.2 | 4.3 ± 1.3 | 1.1 ± 0.7 |
| HA | 48.4 ± 1.2 | 44.6 ± 1.1 | 48.4 ± 1.5 | 49.7 ± 1.1 | 41.5 ± 1.2 | 39.7 ± 1.2 |
| SOFT TISSUE | 51.6 ± 1.2 | 55.4 ± 1.1 | 48.9 ± 1.5 | 50.1 ± 1.1 | 54.3 ± 1.4 | 59.2 ± 1.4 |

Note:
HA = hydroxyapatite framework. Values are given as means ± SEM of 16 granular hydroxyapatite implants and 8 hydroxyapatite rods per group.

TABLE VII

Volume Fraction (%) of Tissue Components in Hydroxyapatite Specimens Implanted in the Rectus Abdominis of 4 Baboons and Harvested at Day 90

| | Granular 200 μm | Granular 500 μm | Rod 200 μm | | Rod 500 μm | |
| --- | --- | --- | --- | --- | --- | --- |
| | | | Level b | Level c | Level b | Level c |
| BONE | 0.0 | 0.1 ± 0.6 | 4.7 ± 1.6 | 2.3 ± 0.9 | 9.3 ± 2.1 | 2.8 ± 1.1 |
| HA | 49.4 ± 0.8 | 45.6 ± 0.7 | 44.0 ± 1.6 | 47.2 ± 1.5 | 38.6 ± 1.2 | 37.1 ± 1.0 |
| SOFT TISSUE | 50.2 ± 0.8 | 54.3 ± 0.7 | 50.1 ± 1.1 | 50.6 ± 1.2 | 52.1 ± 1.8 | 60.2 ± 1.4 |

Note:
HA = hydroxyapatite framework. Values are given as means ± SEM of 16 granular hydroxyapatite implants and 8 hydroxyapatite rods per group.

The observed difference in the amount of bone between levels in hydroxyapatite rods suggests that there is a gradient of bone distribution within the three dimensional porous spaces of the substratum. Selected specimens were thus re-embedded and serial sections cut the amount of bone (in percent) that formed in hydroxyapatite rods implanted extraskeletally in baboons. As can be seen from FIGS. 8, in none of the eight specimens prepared from implants harvested after one month, could bone formation be detected. However, at two months (60 days) after implantation, an average of 4.2% volume fraction of bone was detected (eight specimens). Twenty-four specimens were analyzed at three months after implantation, fourteen at six months and fifteen at nine months. The % volume fractions of bone were 9.3%, 25.9% and 26.7% respectively.

The binding of recombinant human BMP-4 onto porous hydroxyapatite appears not to be affected by the geometry of the hydroxyapatite substratum since $I^{125}$ radiolabelled human recombinant BMP-4 binds equally well to hydroxyapatite substrata in granular and block configuration (Ripamonti, Paralkar and Reddie, unpublished data). Thus, the observed lack of bone formation in granular hydroxyapatite appears not to be related to a limited adsorption of BMPs onto the granular substratum. Since the surface characteristics are identical for both geometric configurations[54], the results of Example 2 confirm that the expression of the osteogenic phenotype and the differentiation of bone are regulated by the geometry of the substratum. (Previously it was shown that granular hydroxyapatite of 200 μm pore size, even when pretreated with osteogenin, failed to initiate and promote bone differentiation in an orthotopic calvarial model in rodents[55]. Biopsy material obtained after clinical trials in humans also showed lack of bone formation in the granular hydroxyapatite.)

The finding that bone, albeit in negligible amounts (FIG. 6, D), differentiated in two specimens of granular hydroxyapatite, indicates that identical morphogenetic mechanism(s) also occurr in granular hydroxyapatite. This suggests that the geometric configuration of the substratum is potentially capable of overriding the biologic activity of putative BMPs adsorbed onto the granular substratum.

The applicant believes the importance of geometry on the differentiation of bone in hydroxyapatite substrata to be critical. This may have important implications in reconstructive craniofacial surgery. Screening of potential substrata in primates can help tissue engineers to construct substrata and delivery systems with defined geometries and surface characteristics for replacement therapies that are conducive to the initiation and promotion of therapeutic osteogensis.

What is claimed is:

1. A method for evaluating the shape and configuration of a porous hydroxyapatite structure for its osteoconductive or osteoinductive potential, which method comprises:
    implanting the structure extraskeletally into a non-human primate;
    removing the structure from the primate after a predetermined period of time; and
    examining the structure after removal to determine approximately the amount of bone which has formed on or within the structure.

2. A method as claimed in claim 1, wherein the structure is implanted intramuscularly in adult baboons.

3. The method as claimed in claim 2, wherein the primate is a baboon and the step of examining the structure comprises subjecting the structure to histological or histomorphometric analysis.

4. The method of claim 1, further comprising the step of, before the implanting step, selecting a structure having a porosity of between about 200–500 μm.

5. The method of claim 1, wherein the structure is examined after at least approximately 90 days.

6. The method of claim 1, wherein the structure is examined at a central core thereof.

7. A method of inducing bone growth in a site in a primate where bone growth is required, which method comprises the steps of
    selecting a suitable porous hydroxyapatite structure, and implanting the structure at the site extraskeletally.

8. The method of claim 7, wherein the primate is an adult baboon.

9. The method of claim 7, wherein the structure is implanted intramuscularly.

10. The method of claim 5, further comprising the step of, after implanting the structure, waiting at least approximately 90 days for sufficient bone growth to occur.

11. A method of inducing bone growth in a site in a primate where bone growth is required, which method comprises the steps of
    preparing a hydroxyapatite structure to have a suitable shape and a porosity of between about 200–500 μm, and implanting the structure at the site extraskeletally.

12. The method of claim 11, further comprising preparing the structure to be in the shape of a rod having a diameter of between 5–7 mm.

* * * * *

UNITED STATES PATENT AND TRADEMARK OFFICE
CERTIFICATE OF CORRECTION

PATENT NO.    : 5,355,898
DATED         : Oct. 18, 1994
INVENTOR(S)   : Ugo Ripamonti It is certified that an error appears in the above-identified patent and that said Letters Patent is hereby corrected as shown below:

On the title page item [21] should read as follows:

[21] Appl. No. 889,934

Signed and Sealed this

Twelfth Day of September, 1995

Attest:

BRUCE LEHMAN

*Attesting Officer*     *Commissioner of Patents and Trademarks*